United States Patent [19]

Porteous

[11] Patent Number: 5,692,610
[45] Date of Patent: Dec. 2, 1997

[54] METHOD AND APPARATUS FOR SINGLE USE DISPENSER PACKAGING OF DENTAL RETRACTION CORDS

[76] Inventor: Don D. Porteous, 650 Beachport, Port Hueneme, Calif. 93041

[21] Appl. No.: 639,467

[22] Filed: Apr. 29, 1996

Related U.S. Application Data

[63] Continuation of Ser. No. 231,194, Apr. 21, 1994, abandoned.

[51] Int. Cl.⁶ .................. B65D 75/46; B65D 73/00
[52] U.S. Cl. ............. 206/388; 206/63.5; 206/368
[58] Field of Search ............ 53/412, 415; 206/63.5, 206/368, 388, 484

[56] References Cited

U.S. PATENT DOCUMENTS

| | | | |
|---|---|---|---|
| 1,387,839 | 8/1921 | Davis | 206/63.3 X |
| 1,914,836 | 6/1933 | Randall | 206/63.3 |
| 1,962,900 | 6/1934 | Hirsch | 206/63.3 |
| 3,035,691 | 5/1962 | Rasmussen et al. | 206/484 X |
| 3,218,003 | 11/1965 | Bradshaw | 206/484 X |
| 3,246,959 | 4/1966 | Brewer | 206/439 |
| 3,258,312 | 6/1966 | Olsen | 206/459.1 |
| 3,278,013 | 10/1966 | Banks | 206/388 X |
| 3,460,752 | 8/1969 | Langdon | 206/439 |
| 3,552,638 | 1/1971 | Quackenbush | 206/484 |
| 3,627,611 | 12/1971 | Bonk | 206/363 |
| 3,704,096 | 11/1972 | Verses et al. | 206/459.1 |
| 3,740,237 | 6/1973 | Grindrod et al. | 53/412 X |
| 3,768,725 | 10/1973 | Pilaro | 206/439 |
| 3,991,881 | 11/1976 | Augurt | 206/439 |
| 4,091,921 | 5/1978 | Lewis | 206/363 |
| 4,098,577 | 7/1978 | Halpern | 206/459.1 |
| 4,121,714 | 10/1978 | Daly et al. | 206/459.1 |
| 4,168,779 | 9/1979 | Yokokoji et al. | 206/439 |
| 4,206,844 | 6/1980 | Thuramoto et al. | 206/459.1 |
| 4,279,344 | 7/1981 | Holloway, Jr. | 206/484 X |
| 4,579,221 | 4/1986 | Corella | 206/63.5 X |
| 4,693,365 | 9/1987 | Corella | 206/388 X |
| 4,712,572 | 12/1987 | Hovel, III | 206/388 X |
| 4,828,108 | 5/1989 | Roth et al. | 206/368 X |
| 4,828,109 | 5/1989 | Roth et al. | 206/368 X |
| 4,852,728 | 8/1989 | Court | 206/63.5 |
| 4,986,289 | 1/1991 | McWhorter | 206/63.5 X |
| 5,322,077 | 6/1994 | Corella | 206/63.5 X |
| 5,369,936 | 12/1994 | Callahan et al. | 53/415 |

*Primary Examiner*—Horace M. Culver
*Attorney, Agent, or Firm*—Louis J. Bachand

[57] ABSTRACT

Method and apparatus for the packaging of single use quantities of product such as dental retraction cords comprising sheet materials laminated about the product interposed between the sheet materials in a continuous length and severed at the locus of transverse lamination to a single use quantity length.

11 Claims, 2 Drawing Sheets

METHOD AND APPARATUS FOR SINGLE USE DISPENSER PACKAGING OF DENTAL RETRACTION CORDS

REFERENCE TO RELATED APPLICATION

This application is a continuation of my now abandoned application Ser. No. 08/231,194, filed Apr. 21, 1994.

TECHNICAL FIELD

This invention has to do with effective packaging of dental retraction cords for protection against contamination and for dispensing in single use quantities, and with producing the new packaging efficiently. More particularly, the invention relates to methods of economically manufacturing single-use-packaged dental retraction cords, to the single use packages obtained, and to incorporation of identifying information into the packages during manufacture, and the use of the invention methods and packaging with a variety of products.

In a more general aspect the invention relates to packaging for single use quantities of product such as dental retraction cords comprising sheet materials laminated about the product interposed between the sheet materials in a continuous length and severed at the locus of transverse lamination to a single use quantity length.

BACKGROUND

Dental retraction cords are lengths of cord impregnated with drugs such as epinephrine and alum, and used to retract the gums from a tooth being treated by a dentist e.g. in preparation for the fitting of a crown. Such cords are typically of short length, between about ¾ inch to about 2 inches, which are wrapped around the tooth at and below the gum line. It has been the practice to furnish dental retraction cords in dispensing containers where a relatively long length of cord is wound on a spool for dispensing and cutting to a single use length at the time of application. More recently, a focus in public health has been on minimizing the possibilities of cross-contamination in dental operatories. Thus the old style dispenser of dental retraction cord, which subsumes the possibility of a number of people handling the cord before it is used on the patients, is desirably supplanted by a supply of cord in which the cord used on the patient is individuated in single use packages and thereby avoids the cross-contamination possibilities found in the old style packaging.

SUMMARY OF THE INVENTION

It is an object therefore of the present invention to provide a novel means of packaging dental retraction cords for individual use. It is another object to provide an efficient manufacturing method for manufacture of single use dental retraction cord packaging. It is another object to provide various means of incorporating information, such as dental/medical descriptions into the packaging. Yet another object is provision of a single use packaging system for products of enhanced efficiency in production and use.

These and other objects to become apparent hereinafter are realized in accordance with the invention by single use dispenser packaging for dental retraction cords comprising first and second sheet materials, and a dental retraction cord interposed therebetween, the first and second sheet materials being laminated about the dental retraction cord in cord contamination blocking relation, i.e. preventing contamination of the cord while packaged, the cord and sheet materials being cut to a length corresponding to the single use quantity of dental retraction cord, e.g. a length between ¾ inch and about 2 inches depending on the tooth to be treated.

In this and like embodiments, the first sheet material is typically cellulosic, e.g. a kraft paper or synthetic paper; the second sheet material is typically plastic, e.g. a colorless and transparent film made from suitable plastic resins such as olefin plastics, polyethylene, polypropylene, vinyl acetates and ionomers, and copolymers thereof, and polyesters such as polyethylene terephthlate.

These sheet materials are locally laminated closely about but not atop the dental retraction cord, other than at the fore and aft terminals of the cord and sheet materials, considered longitudinally, and preferably inward of at least one lateral edge margin of the first and second sheet materials, considered transversely, to facilitate gripping then peeling apart of the laminated first and second sheet materials to free the retraction cord for use.

In certain embodiments of the invention there is further provided an identifying strip co-packaged with the dental retraction cord for purposes of identifying the cord impregnated drug and its dosage in the within dental retraction cord. The present manufacturing method incorporates this added feature with little modification or increase in cost.

Typically, the first and second sheet materials and the dental retraction cord lie elongated and flat within parallel planes, the cord and sheet materials being longitudinally coterminous such that the dental retraction cord extends through the locus of lamination of the first and second sheets to the longitudinal terminus of the first and second sheets with the fore and aft ends of the cord pinned in place by a transverse area of laminate, the cord center portion being free of attachment to either sheet material.

The invention provides in one embodiment a single use dispenser package comprising first and second sheet materials laminated together about single use quantity of product, and an identifying strip co-packaged with the product.

The invention further contemplates the method of manufacturing a severable series of dispensers of single use quantities of dental retraction cord, including passing opposed sheet material lengths along a common path, interposing a dental retraction cord between the sheets, and periodically laminating the sheets together in enclosing relation to lengths of dental retraction cord corresponding to a single use quantity, and cutting the laminated sheet materials and cord transversely to terminate the lengths of dental retraction cord while maintaining them sterilely packaged, and, where sheet material width permits, cutting longitudinally between adjacent one of plural rows of dental retraction cord while maintaining the sheets laminated together about the severed lengths of dental retraction cord in contamination blocking relation.

The invention method typically further includes selecting paper as the first sheet material, and plastic as the second sheet material, and preferably defining a locus of lamination narrower than the cut first and second sheet materials, whereby the edge margins of the first and second sheet materials are unlaminated and can readily be separately grasped to peel apart the first and second sheet materials.

In a further embodiment, the invention provides a method of manufacturing a severable series of dispensers of single use quantities of dental retraction cord, including passing opposed sheet material lengths along a common path, interposing a dental retraction cord between the sheets, interposing an identifying strip between the sheets parallel to the dental retraction cord, and periodically laminating the sheets together in enclosing relation to the identifying strip and to lengths of the dental retraction cord corresponding to single use quantity.

In a still further embodiment, the invention provides a method of manufacturing a severable series of dispensers for single use dispensable product, including passing opposed sheet material lengths along a common path, interposing the dispensable product and an identifying strip between the sheets, and periodically laminating the sheets together in enclosing relation to the product and identifying strip.

In a further aspect, the invention provides a method of manufacturing a continuous length of severable single use dispenser packages of dental retraction cord, including advancing an elongated first sheet material along a predetermined path, laying a continuous length of dental retraction cord on the first sheet material to be advanced along the predetermined path with the first sheet material, advancing an elongated second sheet material along the predetermined path and onto the first sheet material in longitudinal and transverse registration with the first sheet material, longitudinally laminating the first and second sheet materials together on either side of the dental retraction cord, and transversely laminating the first and second sheet materials together across the dental retraction cord at predetermined intervals corresponding to a desired length of dental retraction cord, the first and second sheet materials laminate and dental retraction cord being severable at the predetermined intervals.

BRIEF DESCRIPTION OF THE DRAWINGS

The invention will be further described as to an illustrative embodiment in conjunction with the attached drawings in which.

DETAILED DESCRIPTION

Figure 1:
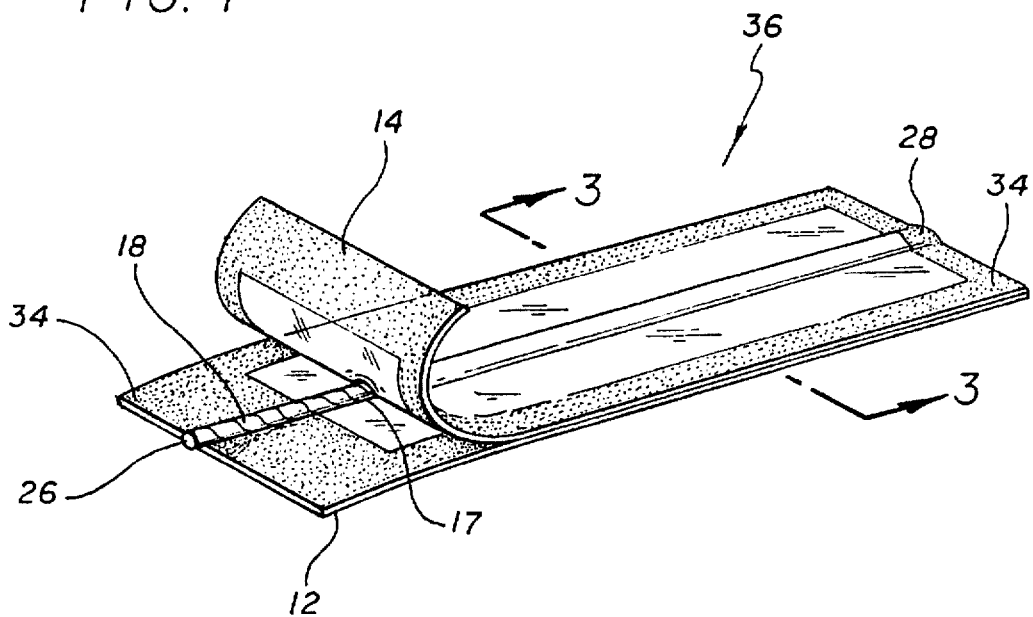
FIG. 1 is an axonometric view of a single use package for dental retraction cord manufactured according to the invention.
Figure 2:
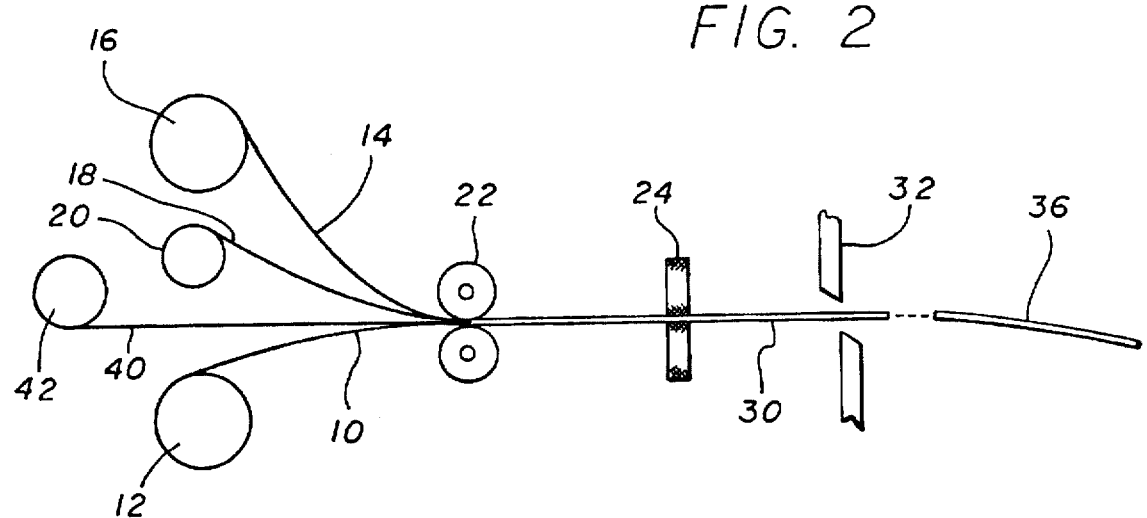
FIG. 2 is a schematic view of a manufacturing line for the invention packaging.
Figure 3:
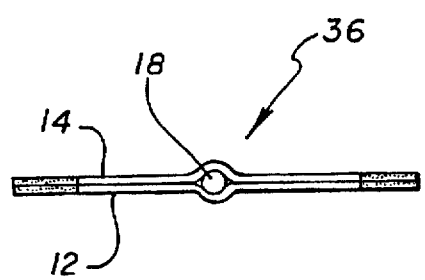
FIG. 3 is a view taken on line 3—3 in FIG. 1.

With reference now to FIGS. 1, 2 and 3 of the drawings in detail, in FIG. 2 a manufacturing line is depicted in which a first paper sheet material 10 is unrolled from a supply 12, a second plastic film sheet material 14 is unrolled from a supply 16, and advanced for longitudinal and transverse registration with the sheet material 10, and dental retraction cord 18 is unrolled from a supply 20 and interposed between the first and second sheet materials, all being drawn in juxtaposed relation by a pair of nip rolls 22. The dental retraction cord supply roll 20 is representative of one, two or more such rolls, whereby, assuming suitable widths of sheet materials 10 and 14 being available on supply rolls 12 and 16, or iterations of such rolls, plural rows of dental cord 18 arranged in parallel to each other may be interposed between sheet materials 10 and 14. The juxtaposed sheet materials 10, 14 and cord 18 are passed to a sealing station 24 where the sheet materials are laminated to each other, with heat and/or adhesive or other agent which seals the two sheet materials to each other, in a pattern continuous about the dental retraction cord, See FIG. 1, by surrounding the retraction cord with laminated sheet material while not laminating the sheet materials at the locus of the dental retraction cord center portion 17, that is atop the cord, except at the longitudinal fore and aft terminals 26, 28 of the cord. After lamination, the resulting assembly 30 is passed to a cutter 32 where the assembly is severed transversely by cutting through the transversely disposed seal area 34 (FIG. 1) which registers with the desired length of the packaged retraction cord sections, forming an individual package 36 containing sufficient dental retraction cord 18 for a single use in the dental operatory. As noted above, the single use length may be varied depending on the intended use.

Figure 5:
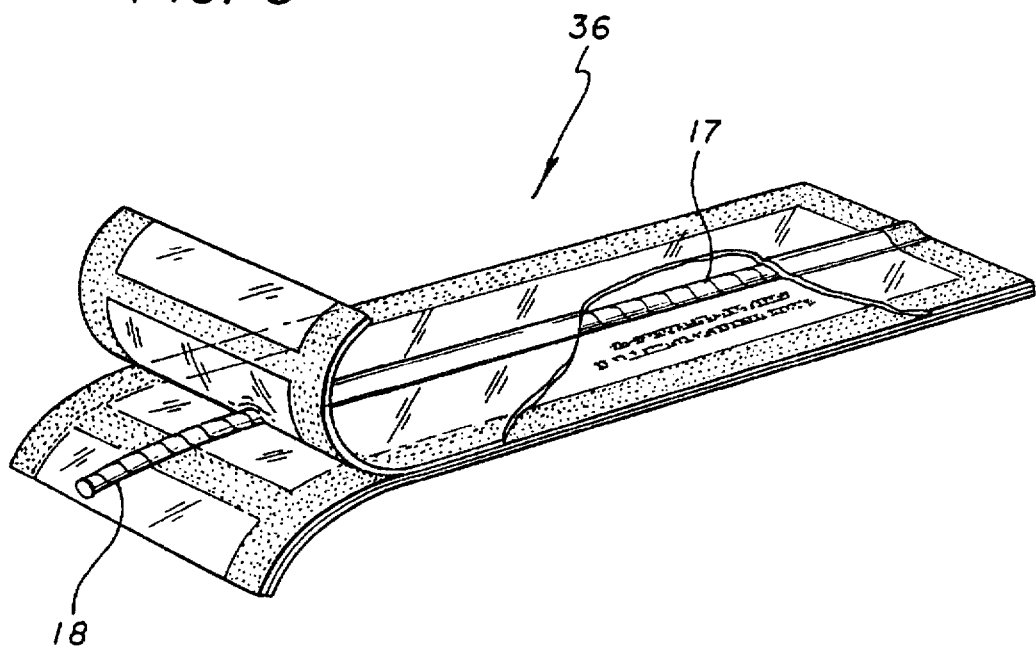
FIG. 5 is a view like FIG. 1 illustrating a further embodiment of the invention in which an identifying strip is incorporated into the packaging.

In a modification of the manufacturing method and product, and with reference again to FIG. 2, an identifying strip 40 may be fed with the sheet materials 10 and 14 and dental retraction cord 18, from supply 42, and laminated therewith, in the manner of the dental retraction cord 18, as best shown in FIG. 5, for purposes of having use expiration times, application requirements, brand indicia, advertising or other information, such as, particularly, the drug and dosage impregnated in the dental retraction cord immediately identifiable. While this same information could be printed or otherwise permanently added to the sheet materials 10 or 14, such practice requires maintaining inventories of differently printed sheet materials 10, 14 corresponding to each drug and dosage used in the dental retraction cords.

Figure 4:
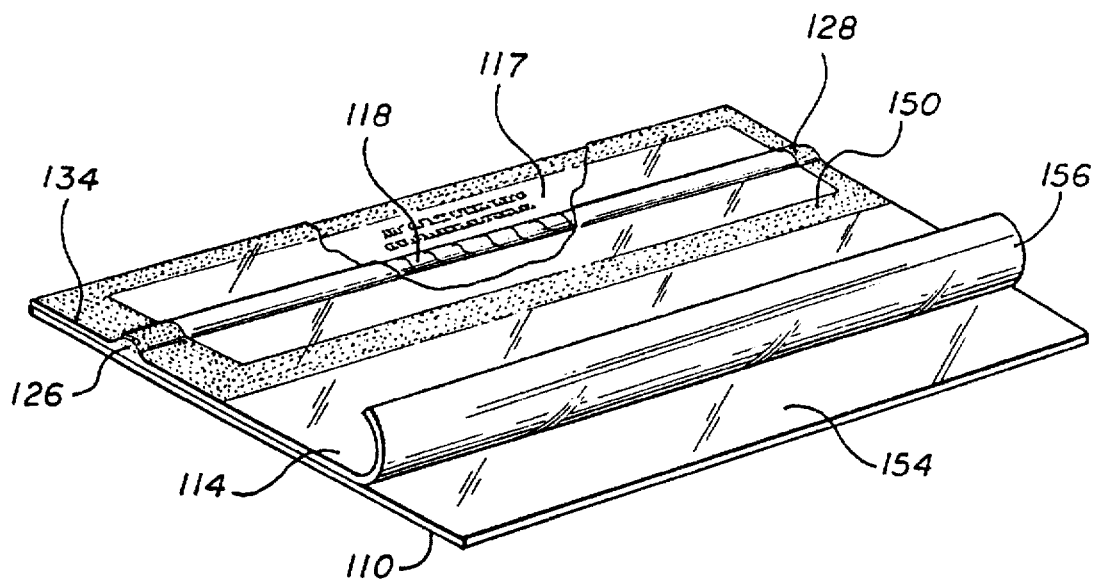
FIG. 4 is a view like FIG. 1 illustrating a single use package wherein the first and second sheet materials each have a free edge margin for grasping to separate the sheet materials and facilitate opening the package.

In a preferred form of the invention, illustrated in FIG. 4, in which like parts bear like numerals to the other Figures, plus 100, the sheet materials 110, 114 are substantially wider than required to enclose the dental retraction cord 118, and the longitudinal seal 150 resulting from lamination of the sheet materials together is set inward a substantial distance on the edge margins 154, 156 on one side of the sheet materials. In this manner, the upper and lower sheet materials edge margins 154, 156 are free of attachment outward beyond the longitudinal seal 150 and may be freely separated, as indicated, and grasped and pulled apart, to facilitate separation of the sheet materials 110, 114 at the seal 150 and all across the seal area 134, making opening the package 136 easier. In addition, useful information can be printed on the now greater surface area available for printing compared with the FIG. 1 embodiment.

While the invention has been particularly described in connection with the single use packaging of dental retraction cord, other dental/medical and like or unlike products capable of being fed in interposed relation with sheet materials, and usefully dispensed in single use packages while being protected against contamination and spoilage by joint cut-off of product and package can be packaged according to the invention by substituting a supply of the product to be packaged for the dental retraction cord supply 20.

Thus the foregoing objects are met including provision of a novel means of packaging dental retraction cords for individual use, an efficient manufacturing method for manufacture of single use dental retraction cord packaging, including means for incorporating information, such as dental/medical descriptions into the packaging, and more generally, the provision of a single use packaging system for products of enhanced efficiency in production and use.

I claim:

1. Single-use dispenser packaging for dental retraction cords comprising first and second sheet materials separably laminated to each other about a straight extent of dental retraction cord, said sheet materials and cord being simultaneously cut following lamination to the same predetermined length corresponding to a single-use length of dental retraction cord providing said sheet materials with fore and aft edges and providing said length of cord with fore and aft ends, said cord fore and aft ends being as far apart as possible and in coterminous condition with said sheet materials fore and aft edges, said cord fore and aft ends being laminated to said fore and aft edges of at least one of said sheet materials in their coterminous condition.

2. Single use dispenser packaging according to claim 1, in which said first sheet material is cellulosic.

3. Single use dispenser packaging according to claim 1, in which said second sheet material is plastic.

4. Single use dispenser packaging according to claim 1, in which said sheet materials are locally laminated closely about said dental retraction cord and inward of at least one lateral edge of said first and second sheet materials to facilitate gripping and peeling apart of said first and second sheet materials.

5. Single use dispenser packaging according to claim 1, including also an identifying strip co-packaged between said first and second sheet materials with said dental retraction cord.

6. Single use dispenser package according to claim 1, in which said dental retraction cord extends between said separably laminated first and second sheets to said fore and aft edges of said first and second sheets, said cord being straight throughout its extent so that its fore and aft ends are as far from each other as possible.

7. Single use dispenser packaging for dental retraction cords comprising first and second sheet materials, and a single use length of dental retraction cord interposed therebetween, said single length of dental retraction cord having opposite cord ends and a cord center portion therebetween, said first and second sheet materials being separably laminated to each other peripherally about said dental retraction cord in cord end adhering relation when said sheet materials are separated, the cord center portion being free of attachment to said sheet materials, said first and second sheet materials and said dental retraction cord lying elongated and flat within parallel planes, said cord and sheet materials being longitudinally coterminous, whereby said cord ends are pinned to at least one of said sheet materials when said sheet materials are separated.

8. Single use dispenser packaging according to claim 6, in which said first sheet material is cellulosic.

9. Single use dispenser packaging according to claim 8, in which said second sheet material is plastic.

10. Single use dispenser packaging according to claim 9, in which said sheet materials are locally laminated closely about said dental retraction cord and inward of at least one lateral edge of said first and second sheet materials to facilitate gripping and peeling apart of said first and second sheet materials.

11. Single use dispenser packaging according to claim 10, including also an identifying strip co-packaged between said first and second sheet material with said dental retraction cord.

* * * * *